United States Patent
De Silva et al.

(10) Patent No.: US 12,338,208 B2
(45) Date of Patent: Jun. 24, 2025

(54) FLUID CATALYTIC CRACKING CATALYST COMPOSITION FOR ENHANCED BUTYLENE TO PROPYLENE SELECTIVITY RATIO

(71) Applicant: BASF CORPORATION, Florham Park, NJ (US)

(72) Inventors: Wathudura Indika Namal De Silva, Iselin, NJ (US); David M. Stockwell, Iselin, NJ (US); Bilge Yilmaz, Iselin, NJ (US); Junmei Wei, Iselin, NJ (US)

(73) Assignee: BASF Corporation, Florham Park, NJ (US)

( * ) Notice: Subject to any disclaimer, the term of this patent is extended or adjusted under 35 U.S.C. 154(b) by 152 days.

(21) Appl. No.: 18/017,775

(22) PCT Filed: Jul. 30, 2021

(86) PCT No.: PCT/US2021/043979
§ 371 (c)(1),
(2) Date: Jan. 24, 2023

(87) PCT Pub. No.: WO2022/026878
PCT Pub. Date: Feb. 3, 2022

(65) Prior Publication Data
US 2023/0192573 A1 Jun. 22, 2023

Related U.S. Application Data

(60) Provisional application No. 63/059,227, filed on Jul. 31, 2020.

(51) Int. Cl.
*C07C 4/06* (2006.01)
*B01J 21/04* (2006.01)
(Continued)

(52) U.S. Cl.
CPC .............. *C07C 4/06* (2013.01); *B01J 21/04* (2013.01); *B01J 23/10* (2013.01); *B01J 29/084* (2013.01);
(Continued)

(58) Field of Classification Search
None
See application file for complete search history.

(56) References Cited

U.S. PATENT DOCUMENTS 4,740,292 A   4/1988   Chen et al.
5,314,612 A   5/1994   Eberly et al.
(Continued)

FOREIGN PATENT DOCUMENTS

WO   2010077537 A2   7/2010
WO   2014042641 A1   3/2014

OTHER PUBLICATIONS

European Search Report for EP Patent Application No. 21850805.9, Issued on Jul. 10, 2024, 3 pages.
(Continued)

*Primary Examiner* — Tam M Nguyen
(74) *Attorney, Agent, or Firm* — Peter T. DiMauro

(57) ABSTRACT

Disclosed herein is a fluid catalyst cracking (FCC) catalyst composition that includes a first component and a second component. The first component and second component may be separate microspheroidal FCC catalysts or may be incorporated in a common microspheroidal FCC catalyst. The first component includes zeolite Y and a first matrix that includes gamma-alumina. The second component includes beta zeolite and a second matrix. Also disclosed herein are methods of preparing the FCC catalyst composition and method of using the FCC catalyst composition.

20 Claims, 1 Drawing Sheet

(51) Int. Cl.
B01J 23/10        (2006.01)
B01J 29/04        (2006.01)
B01J 29/08        (2006.01)
B01J 29/70        (2006.01)
B01J 29/80        (2006.01)
B01J 35/51        (2024.01)
B01J 35/61        (2024.01)
B01J 29/06        (2006.01)

(52) U.S. Cl.
CPC ........... *B01J 29/7007* (2013.01); *B01J 35/51* (2024.01); *B01J 35/613* (2024.01); *B01J 35/615* (2024.01); *B01J 2029/062* (2013.01); *C07C 2521/04* (2013.01); *C07C 2523/10* (2013.01); *C07C 2529/08* (2013.01); *C07C 2529/70* (2013.01); *C07C 2529/80* (2013.01)

(56) References Cited

U.S. PATENT DOCUMENTS

| | | |
|---|---|---|
| 2008/0293561 A1 | 11/2008 | Long et al. |
| 2008/0314798 A1* | 12/2008 | Stockwell ............ B01J 37/0246 502/73 |
| 2013/0066131 A1 | 3/2013 | Harris |
| 2015/0174560 A1* | 6/2015 | McGuire, Jr. ........ B01J 37/0201 502/80 |
| 2015/0175899 A1* | 6/2015 | McGuire, Jr. .......... B01J 29/088 208/114 |
| 2015/0175900 A1* | 6/2015 | Smith ...................... B01J 21/02 502/68 |
| 2018/0237702 A1* | 8/2018 | Akah ..................... B01J 29/084 |
| 2018/0272324 A1* | 9/2018 | Ravishankar ........ B01J 37/0201 |
| 2019/0062641 A1* | 2/2019 | Medellin Rivera .... B01J 29/088 |
| 2020/0078774 A1* | 3/2020 | Wei .......................... B01J 21/04 |
| 2023/0294083 A1* | 9/2023 | De Silva ................. B01J 21/02 208/120.01 |
| 2023/0398525 A1* | 12/2023 | Stockwell ................ B01J 37/28 |
| 2024/0001351 A1* | 1/2024 | Yilmaz .................. C10G 11/18 |

OTHER PUBLICATIONS

International Search Report and Written Opinion of International Application No. PCT/US2021/043979 mailed Dec. 14, 2021, 9 pgs.

* cited by examiner

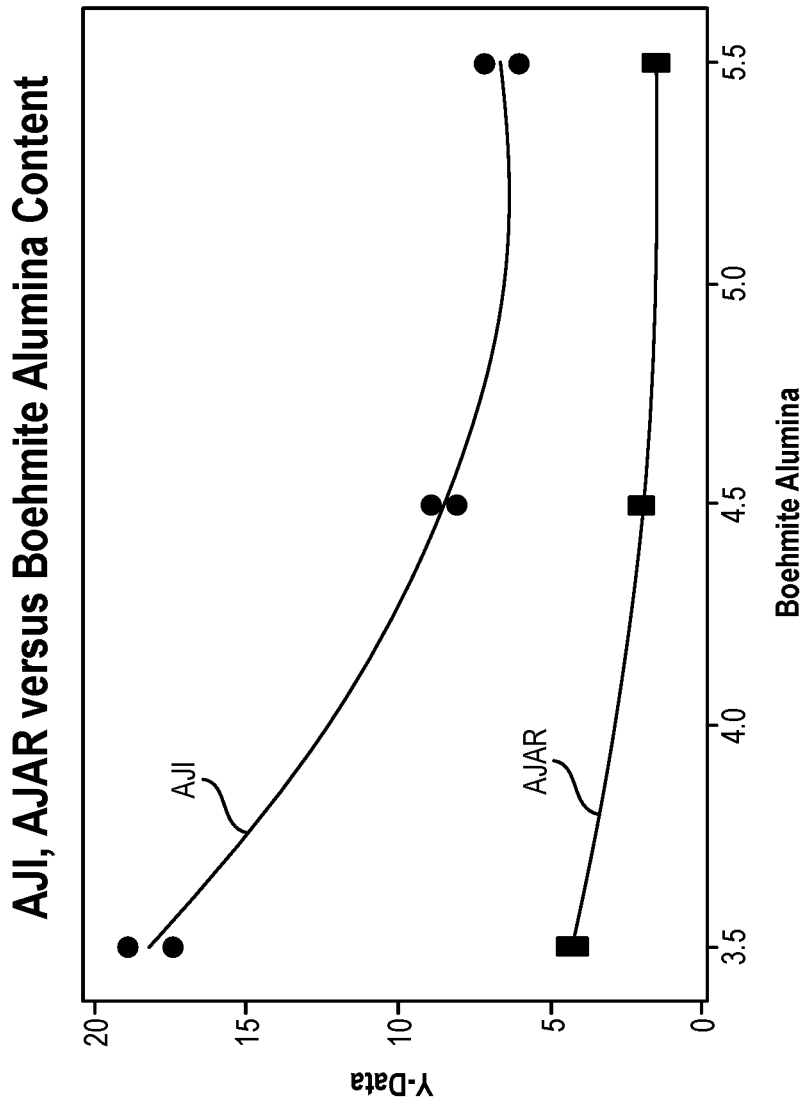

FLUID CATALYTIC CRACKING CATALYST COMPOSITION FOR ENHANCED BUTYLENE TO PROPYLENE SELECTIVITY RATIO

CROSS-REFERENCE TO RELATED APPLICATION(S)

This application claims the benefit of priority of U.S. Provisional Patent Application No. 63/059,227, filed on Jul. 31, 2020, the disclosure of which is hereby incorporated by reference herein in its entirety.

FIELD OF THE DISCLOSURE

The present disclosure relates to petroleum refining catalysts and compositions thereof. In particular, the present disclosure relates to fluid catalytic cracking (FCC) catalysts and compositions thereof, methods of their preparation, and methods of their use.

BACKGROUND OF THE DISCLOSURE

FCC is the main source of the world's butylenes production. Almost half of the butylenes production is sourced from FCC units, and more than 40% of it is consumed to make high octane blending components via alkylation units. Due to increasing demand for improved fuel efficiency, more and more refiners find it profitable to increase butylenes in their units. However, conventional olefin maximization additives based on ZSM-5 alone are not sufficient to meet this target. ZSM-5 additives are designed to make propylene; thus, they make more propylene over butylenes. When the units are wet-gas compressor limited the use of ZSM-5 will increase propylene more than butylenes, thus reaching the liquefied petroleum gas (LPG) limit constraints before reaching the required butylenes yields. In such a scenario the unit needs a catalyst (or additive) solution which contributes to increased butylenes/propylene (C4=/C3=) ratio compared to ZSM-5.

SUMMARY OF THE DISCLOSURE

The present disclosure provides a fluid catalytic cracking (FCC) catalyst composition that includes a first component and a second component. The first component includes Y zeolite and a first matrix that includes gamma-alumina. The second component includes beta zeolite and a second matrix. At least one additional component that is compositionally different from the first component and from the second component may also be included in the FCC catalyst composition. The composition of the various components provides for an FCC catalyst composition that includes multiple zeolitic frameworks to deliver superior butylenes activity, butylenes yield, and butylenes selectivity, while maintaining constant or lower yields and selectivity for less desired products, such as coke and bottoms.

The first component and the second component may be a first and a second FCC microspheroidal catalysts, respectively. The first component may be present in the FCC catalyst composition in a greater amount than the second component. For instance, the weight to weight ratio of the first component to the second component in the FCC catalyst composition may range from about 10:1 to about 1.5:1, from about 8:1 to about 2:1, or from about 4:1 to about 3:1.

The first component includes Y zeolite and a first matrix that may include, in addition to gamma-alumina, clay, rare earth-doped alumina (e.g., one or more of ytterbium-doped alumina, gadolinium-doped alumina, cerium-doped alumina, or lanthanum-doped alumina), $SiO_2$—$Al_2O_3$ matrix, silica-doped alumina, $\chi$-alumina, $\delta$-alumina, $\theta$-alumina, $\kappa$-alumina, boehmite, or a combination of two or more thereof.

The second component includes beta zeolite and a second matrix. The beta zeolite in the second component may have a SAR ranging from about 20 to about 300, about 25 to about 100, about 30 to about 50, or about 30 to about 40.

In certain embodiments, during preparation of the second component, phosphoric acid may be added to form a second component that contains oxidized phosphorus. The phosphorus may be present in a second component (formed with the addition of phosphoric acid) as $AlPO_4$, on the beta zeolite, and/or as polyphosphates. Second components formed with the addition of phosphoric acid may be referred to herein as "second component with oxidized phosphorus." Reference to the oxidized phosphorus in the second component may also be referred to herein as "$P_2O_5$."

In certain embodiments, during preparation of the second component, silica-alumina binder treated with ammonium phosphate may be added, as described in U.S. Pat. No. 8,940,652 B2, incorporated herein by reference in its entirety) to form a phosphorus treated (PT) second component. Second components formed with silica-alumina binder treated with ammonium phosphate may be referred to herein as "phosphorus treated (PT) second component."

In certain embodiments, during preparation of the second component, silica-alumina binder that was not treated with ammonium phosphate ($SiO_2$) may be added. Second components formed with silica-alumina binder without ammonium phosphate treatment may be referred to herein as "second component with $SiO_2$ binder."

When the second component includes a phosphate based constituent (e.g., oxidized phosphorus or PT), the second component may be substantially free of gamma-alumina. It is believed that the combination of a phosphate based constituent with gamma-alumina adversely affect the activity of the second component.

The second component may also include $AlPO_4$ generated due to the interaction of boehmite, added during the preparation of the second component, and a phosphate based constituent (such as oxidized phosphorus (e.g., $P_2O_5$)). The amount of boehmite added during the preparation process and correspondingly the $AlPO_4$ content in the second component may contribute to the attrition resistance of the second component.

The beta zeolite structure, activity, and attrition resistance of the second component may be evidenced by one or more of the following properties: zeolite surface area (ZSA), steamed zeolite surface area (ZSA), Brönsted acidity, TC4= (Total butylenes) yield, dose of second component required to achieve an incremental increase of 0.5 wt % (or 1 wt %) of TC4=yield, butylenes to propylene selectivity ratio, coke and bottoms yield and selectivity, and the like. Hence, in various embodiments described herein, the instant disclosure is directed to an FCC catalyst composition that includes a second component having the values described herein for these properties. These values should be viewed as target achievable values and not inherent to the second components described herein.

Also contemplated herein, in certain embodiments, is a common component that includes Y zeolite, beta zeolite, and gamma-alumina. In such arrangement, the common component may be substantially free of a phosphate based constituent.

In certain aspects, the instant disclosure is directed to a method of making an FCC catalyst composition by blending any of the first components described herein with any of the second components described herein. The method may further include adding to the FCC catalyst composition at least one additional component that is compositionally different from the first component and from the second component. The method may further include preparing one or more of: the first component, the second component, and/or the at least one additional component prior to blending the various components together.

In certain aspects, the instant disclosure is directed to a method of cracking a hydrocarbon feed by contacting said feed with any of the FCC catalyst compositions described herein. The method results in a higher total butylenes yield (TC4=yield) while maintaining a similar yield and selectivity for less desired products (e.g., coke and bottoms) and a preferential butylenes to propylene selectivity ratio, as compared to FCC catalyst compositions that do not have either the first component or the second component.

In at least one aspect, a fluid catalytic cracking (FCC) catalyst composition comprises a first component comprising Y zeolite and a first matrix comprising gamma-alumina; and a second component comprising beta zeolite and a second matrix.

In at least one embodiment, the first component comprises an incorporated catalyst or an in-situ catalyst.

In at least one embodiment, the first component is a first microspheroidal FCC catalyst that is present in the FCC catalyst composition in an amount ranging from about 10 wt % to about 90 wt %, from about 30 wt % to about 80 wt %, or from about 50 wt % to about 70 wt %, based on total weight of the FCC catalyst composition.

In at least one embodiment, the second component is a second microspheroidal FCC catalyst that is present in the FCC catalyst composition in an amount ranging from about 0.1 wt % to about 20 wt %, from about 1 wt % to about 15 wt %, or from about 2 wt % to about 10 wt %, based on total weight of the FCC catalyst composition.

In at least one embodiment, the first component comprises at least about 10 wt %, at least about 30 wt %, or at least about 60 wt % Y zeolite, based on total weight of the first component.

In at least one embodiment, the first component comprises about 1 wt % to about 80 wt %, about 5 wt % to about 60 wt %, or about 10 wt % to about 40 wt % gamma-alumina, based on total weight of the first component.

In at least one embodiment, the second component comprises at least about 10 wt % to about 60 wt %, about 15 wt % to about 55 wt %, about 20 wt % to about 50 wt %, or about 25 wt % to about 45 wt % beta zeolite, based on total weight of the second component.

In at least one embodiment, the second component comprises $AlPO_4$.

In at least one embodiment, the second component comprises $AlPO_4$ at an amount of about 1 wt % to about 25 wt %, about 5 wt % to about 23 wt %, or about 7 wt % to about 20 wt %, based on total weight of the second component.

In at least one embodiment, the second component further comprise one or more of oxidized phosphorus, phosphate treated component, or a silica-alumina binder.

In at least one embodiment, the second component comprises $P_2O_5$.

In at least one embodiment, the second component comprises about 1 wt % to about 30 wt %, about 2 wt % to about 25 wt %, or about 5 wt % to about 20 wt % $P_2O_5$, based on total weight of the second component.

In at least one embodiment, the second component is substantially free of gamma-alumina.

In at least one embodiment, the second matrix comprises kaolin.

In at least one embodiment, the silica to alumina ratio (SAR) in the beta zeolite ranges from about 20 to about 300, from about 25 to about 100, from about 30 to about 50, or about 30 to about 40.

In at least one embodiment, the zeolite surface area (ZSA) of the second component ranges from about 50 $m^2/g$ to about 300 $m^2/g$, from about 75 $m^2/g$ to about 200 $m^2/g$, from about 100 $m^2/g$ to about 180 $m^2/g$, from about 120 $m^2/g$ to about 170 $m^2/g$, or from about 110 $m^2/g$ to about 130 $m^2/g$.

In at least one embodiment, the steamed zeolite surface area (SZSA) of the second component ranges from ranges from about 50 $m^2/g$ to about 300 $m^2/g$, from about 75 $m^2/g$ to about 140 $m^2/g$, from about 90 $m^2/g$ to about 120 $m^2/g$, or from about 100 $m^2/g$ to about 110 $m^2/g$, after steaming in 100% steam at 1450° F. for 24 hours.

In at least one embodiment, at least about 65%, at least about 70%, at least about 75%, at least about 80%, at least about 90%, or about 80% to about 90% of the ZSA of the second component is maintained after steaming in 100% steam at 1450° F. for 24 hours.

In at least one embodiment, the Brönsted acidity of the second component ranges from about 10 μmol/g to about 65 μmol/g, from about 25 μmol/g to about 60 μmol/g, or about 35 μmol/g to about 55 μmol/g.

In at least one embodiment, the air jet attrition rate (AJAR) of the second component is less than about 5 wt %/hr, less than about 4.5 wt %/hr, or less than about 4 wt %/hr.

In at least one embodiment, the first matrix further comprises one or more of clay, rare earth-doped alumina, $SiO_2$—$Al_2O_3$ matrix, and silica-doped alumina, χ-alumina, δ-alumina, θ-alumina, κ-alumina, or boehmite.

In at least one embodiment, the rare earth-doped alumina is selected from one or more of ytterbium-doped alumina, gadolinium-doped alumina, cerium-doped alumina, or lanthanum-doped alumina. In at least one embodiment, the rare earth-doped alumina is lanthanum-doped alumina.

In at least one embodiment, the gamma-alumina further comprises an alkaline earth element.

In at least one embodiment, the alkaline earth element comprises one or more of barium, calcium, or magnesium.

In at least one embodiment, the gamma-alumina further comprises a rare earth element. In at least one embodiment, the rare earth element comprises one or more of ytterbium, gadolinium, cerium, or lanthanum.

In at least one embodiment, the gamma-alumina comprises the alkaline earth element and/or the rare earth element in an amount of about 0.1 wt % to about 12 wt % or about 1 wt % to about 10 wt %.

In at least one embodiment, the first matrix further comprises kaolin that has been subjected to calcination through an exotherm.

In at least one embodiment, the Y zeolite in the first component comprises Y zeolite that has been ion-exchanged to reduce the sodium content to less than 0.7 wt %, or to less than 0.5 wt % $Na_2O$, based on total weight of the ion-exchanged Y zeolite.

In at least one embodiment, the Y zeolite in the first component comprises Y zeolite that has been ion exchanged to include a rare earth element.

In at least one embodiment, the rare earth element in the rare earth element ion-exchanged Y zeolite comprises one or more lanthanum, cerium, praseodymium, neodymium, or yttrium.

In at least one embodiment, the FCC catalyst composition further comprises at least one additional component that is compositionally different from the first component and from the second component.

In at least one embodiment, the at least one additional component comprises a zeolite selected from ZSM-5, mordenite, ferrierite, MCM-22, MCM-68, Y zeolite, beta zeolite, or a combination thereof.

In at least one embodiment, the at least one additional component comprises ZSM-5 zeolite.

In at least another aspect, a method of making an FCC catalyst composition comprises blending a first component and a second component. In at least one embodiment, the first component comprises Y zeolite and a first matrix comprising gamma-alumina, and the second component comprises beta zeolite and a second matrix.

In at least one embodiment, the first component is a first microspheroidal FCC catalyst that is present in the FCC catalyst composition in an amount ranging from about 10 wt % to about 90 wt %, from about 30 wt % to about 80 wt %, or from about 50 wt % to about 70 wt %, based on total weight of the FCC catalyst composition.

In at least one embodiment, the second component is a second microspheroidal FCC catalyst that is present in the FCC catalyst composition in an amount ranging from about 0.1 wt % to about 20 wt %, from about 1 wt % to about 15 wt %, or from about 2 wt % to about 10 wt %, based on total weight of the FCC catalyst composition.

In at least one embodiment, the method further comprises forming the first component by incorporation or in-situ. In at least one embodiment, forming the first component in-situ comprises: pre-forming first precursor microspheres comprising the first matrix; and in-situ crystallizing zeolite Y inside the pre-formed first precursor microspheres to form the first microspheroidal FCC catalyst. In at least one embodiment, the in-situ crystallizing comprises: mixing the pre-formed first precursor microspheres with sodium silicate, sodium hydroxide, and water to obtain an alkaline slurry; and heating the alkaline slurry to a temperature, and for a time, sufficient to crystallize at least about 15 wt % NaY-zeolite, or at least about 40 wt % in or on the pre-formed first precursor microspheres, based on total weight of the pre-formed first precursor microspheres.

In at least one embodiment, the first matrix comprises gamma-alumina and optionally one or more of clay, rare earth-doped alumina, $SiO_2$—$Al_2O_3$ matrix, and silica-doped alumina, χ-alumina, δ-alumina, θ-alumina, κ-alumina, or boehmite.

In at least one embodiment, the method further comprises: separating a first zeolitic microspheroidal material from at least a major part of the alkaline slurry; exchanging sodium cations in the first zeolitic microspheroidal material with ammonium ions or ammonium ions and thereafter rare earth ions.

In at least one embodiment, the method further comprises: calcining the first zeolitic microspheroidal material; further exchanging the first zeolitic microspheroidal material with ammonium ions such that the $Na_2O$ content is reduced to below 0.2%; and further calcining the first zeolitic microspheroidal material.

In at least one embodiment, forming a second microspheroidal FCC catalyst comprises: slurry blending beta zeolite with a second non-zeolitic material comprising boehmite alumina, and kaolin to form a slurry; and spray drying the slurry to form a second microspheroidal FCC catalyst material.

In at least one embodiment, the method further comprises adding phosphoric acid during the spray drying.

In at least one embodiment, the method further comprises calcining the spray dried, and optionally oxidized phosphorus containing, second microspheroidal FCC catalyst material, to form the second microspheroidal FCC catalyst.

In at least another aspect, a method of cracking a hydrocarbon feed comprising contacting said feed with an FCC catalyst composition comprising a first component and a second component. In at least one embodiment, the first component comprises Y zeolite and a first matrix comprising gamma-alumina, and the second component comprises beta zeolite and a second matrix.

In at least one embodiment, the method results in an average butylenes to propylene selectivity ratio of greater than about 0.7, greater than about 0.8, greater than about 0.85, greater than about 0.9, or greater than about 0.95.

In at least one embodiment, the method maintains an average butylenes to propylene selectivity ratio that is within about 5%, within about 10%, or within about 15% of the average butylenes to propylene selectivity ratio obtained when contacting the feed with an FCC catalyst composition that comprises the first component without the second component.

In at least one embodiment, the method results in increase of the total butylenes yield (TC4=) of greater than about 0.2 wt %, greater than about 0.3 wt %, greater than about 0.4 wt %, or greater than about 0.5 wt %, when compared to contacting the feed with an FCC catalyst composition that comprises the first component without the second component.

In at least one embodiment, the method results in constant or lower bottoms versus coke selectivity ratio, when compared to contacting the feed with an FCC catalyst composition that comprises the first component without the second component.

In at least one embodiment, the method results in increase of the total C5=olefins yield (TC5=) when compared to contacting the feed with an FCC catalyst composition that comprises the first component without the second component.

In at least one embodiment, the method results in increase of the total C5=olefins yield (TC5=) of greater than about 0.2 wt %, or greater than about 0.3 wt %, when compared to contacting the feed with an FCC catalyst composition that comprises the first component without the second component.

In at least one embodiment, the method results in increase of the total C5=olefins yield (TC5=) of greater than about 0.2 wt %, or greater than about 0.3 wt %, when compared to contacting the feed with an FCC catalyst composition for which the second component is replaced with ZSM-5.

In at least another aspect, a fluid catalytic cracking (FCC) catalyst comprises: Y zeolite; beta zeolite; and a matrix comprising gamma-alumina. In at least one embodiment, the gamma-alumina is rare earth doped. In at least one embodiment, the matrix further comprises one or more of one or more of clay, rare earth-doped alumina, $SiO_2$—$Al_2O_3$ matrix, silica-doped alumina, χ-alumina, δ-alumina, θ-alumina, κ-alumina, or boehmite. In at least one embodiment, the FCC catalyst is substantially free of phosphate based constituent.

BRIEF DESCRIPTION OF THE DRAWING

The above and other features of the present disclosure, their nature, and various advantages will become more apparent upon consideration of the following detailed description, taken in conjunction with the accompanying drawing, in which:

The FIGURE depicts a scatter plot of attrition jet index (AJI) and air jet attrition rate (AJAR) of the second component as a function of boehmite alumina content (on a volatile-free (VF) basis) used to form the second component.

DEFINITIONS

As used herein, the singular forms "a," "an," and "the" include plural references unless the context clearly indicates otherwise. Thus, for example, reference to "a microsphere" includes a single microsphere as well as a mixture of two or more similar or different microspheres, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±10%, such that "about 10" would include from 9 to 11.

As used herein, the term "catalyst" or "catalyst composition" or "catalyst material" refers to a material that promotes a reaction.

As used herein, the term "fluid catalytic cracking" or "FCC" refers to a conversion process in petroleum refineries wherein high-boiling, high-molecular weight hydrocarbon fractions of petroleum crude oils are converted to more valuable gasoline, olefinic gases, and other products.

As used herein, the term "feed" or "feedstock" refers to that portion of crude oil that has a high boiling point and a high molecular weight. In FCC processes, a hydrocarbon feedstock is injected into the riser section of an FCC unit, where the feedstock is cracked into lighter, more valuable products upon contacting hot catalyst circulated to the riser-reactor from a catalyst regenerator.

As used herein, the terms "non-zeolitic component" or "matrix" refer to the components of an FCC catalyst that are not zeolites or molecular sieves. As used herein, the non-zeolitic component can comprise binder and filler.

As used herein, the term "zeolite" refers to is a crystalline aluminosilicate with a framework based on an extensive three-dimensional network of silicon, aluminum and oxygen ions and have a substantially uniform pore distribution.

As used herein, the term "intergrown zeolite" refers to a zeolite that is formed by an in-situ crystallization process.

As used herein, the term "in-situ crystallized" refers to the process in which a zeolite is grown or intergrown directly on/in a microsphere and is intimately associated with the matrix or non-zeolitic material, for example, as described in U.S. Pat. Nos. 4,493,902 and 6,656,347. The zeolite is intergrown directly on/in the macropores of the precursor microsphere such that the zeolite is intimately associated is uniformly dispersed on the matrix or non-zeolitic material.

As used herein, the term "incorporated catalyst" refers to a process in which the zeolitic component is crystallized and then incorporated into microspheres in a separate step.

As used herein, the terms "preformed microspheres" or "precursor microspheres" refer to microspheres obtained by spray drying and calcining a non-zeolitic matrix component and a gamma-alumina.

As used herein, the term "zeolite-containing microsphere" refers to a microsphere obtained either by in-situ crystallizing a zeolite material on pre-formed precursor microspheres or by microspheres in which the zeolitic component is crystallized separately and then mixed with the precursor microspheres.

"Bottoms" refers to the heaviest fraction of cracked gasoil, also known as heavy cycle oil (HCO), and has very little value. LCO (light cycle oil) is much more valuable since, with further refining, LCO is transformed into diesel fuel. Catalysts that maximize LCO/bottoms ratio as a function of conversion (conversion in FCC is typically defined as 100-LCO-bottoms) are therefore desired.

As used herein, the term "composition" refers to a blend or a mixture of two or more separate and distinct components, such as a first component mixed or blended with a second component. In certain embodiments, the components in the composition are chemically combined and cannot be separated through physical means (e.g., filtration). In other embodiments, the components in the composition are not chemically combined and may be separated through physical means (e.g., filtration).

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

This disclosure is directed in certain embodiments to a fluid catalytic cracking (FCC) catalyst composition that includes a first component and a second component. The first component includes Y zeolite and a first matrix, where the first matrix includes gamma-alumina. The second component includes beta zeolite and a second matrix. In certain embodiments, the first component and the second component may be separate microspheroidal FCC catalysts. In other embodiments, the first component and the second component may be incorporated together in a common microspheroidal FCC catalyst.

This disclosure is also directed in certain embodiments to a method of preparing said FCC catalyst composition, including, in certain embodiments, to methods of preparing each of the first component and the second component. In certain embodiments, this disclosure is directed to a method of preparing said common microspheroidal FCC catalyst.

This disclosure is also directed in certain embodiments to a method of using said FCC catalyst composition and/or said common microspheroidal FCC catalyst when cracking a hydrocarbon feed to increase the total butylenes yield while maintaining a favorable butylenes to propylene selectivity ratio, all without compromising the yield and selectivity of less desirable products, such as bottoms and coke.

Each of the first and second components, along with methods of their preparation, will be described below separately, followed by a description of the FCC catalyst compositions along with a method of its preparation and use.

First Component

In one embodiment, the first component includes a Y zeolite and a first matrix that includes gamma-alumina. The first component may be a first microspheroidal FCC catalyst in certain embodiments though other catalyst shapes may also be suitably used. The first component may be an incorporated catalyst or an in-situ catalyst. In one embodiment, the first component is an incorporated catalyst. In another embodiment, the first component is an in-situ catalyst.

The first component (e.g., first microspheroidal FCC catalyst) may be present in the FCC catalyst composition in an amount ranging from any of about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, or about 90 wt %, based on total weight of the FCC catalyst composition. In certain embodiments, the first component (e.g., first microspheroidal FCC catalyst) is present in the catalyst composition in an amount ranging from about 10 wt % to about 90 wt %, from about 30 wt % to about 80 wt %, from about 50 wt % to about 70 wt %, or any sub-range or single value therein, based on total weight of the FCC catalyst composition.

In some embodiments, the first component (e.g., first microspheroidal FCC catalyst) includes from any of about 1 wt %, about 3 wt %, about 5 wt %, about 8 wt %, about 10 wt %, about 15 wt %, about 20 wt %, or about 25 wt % to any of about 30 wt %, about 35 wt %, about 40 wt %, about 45 wt %, about 50 wt %, about 60 wt %, about 70 wt %, or about 80 wt %, gamma-alumina, based on total weight of the first component. In certain embodiments, the first component includes about 1 wt % to about 80 wt %, about 5 wt % to about 60 wt %, about 10 wt % to about 70 wt %, about 10 wt % to about 40 wt %, or any sub-range or single value therein, based on total weight of the first component. In some embodiments, the first component includes about 1 wt % to about 60 wt % of the gamma-alumina. In some embodiments, the first component includes about 10 wt % to about 40 wt % of the gamma-alumina. In particular embodiments, the first component includes about 30 wt % the gamma-alumina.

In some embodiment described herein, the first component (e.g., first microspheroidal FCC catalyst) or the first matrix may further include clay, rare earth-doped alumina (e.g., selected from one or more of ytterbium-doped alumina, gadolinium-doped alumina, cerium-doped alumina, or lanthanum-doped alumina), $SiO_2$—$Al_2O_3$ matrix, silica-doped alumina, $\chi$-alumina, $\delta$-alumina, $\theta$-alumina, $\kappa$-alumina, boehmite, or mixtures of two or more thereof. In particular embodiments, the first component (e.g., first microspheroidal FCC catalyst) or the first matrix may include a mixture of gamma-alumina and one or more of clay, rare earth-doped alumina (e.g., selected from one or more of ytterbium-doped alumina, gadolinium-doped alumina, cerium-doped alumina, or lanthanum-doped alumina), $SiO_2$—$Al_2O_3$ matrix, silica-doped alumina, $\chi$-alumina, $\delta$-alumina, $\theta$-alumina, $\kappa$-alumina, and boehmite. In some embodiments, the first component (e.g., first microspheroidal FCC catalyst) or first matrix may include a mixture of gamma-alumina, $\chi$-alumina, and one or more of clay, rare earth-doped alumina (e.g., selected from one or more of ytterbium-doped alumina, gadolinium-doped alumina, cerium-doped alumina, or lanthanum-doped alumina), $SiO_2$—$Al_2O_3$ matrix, silica-doped alumina, $\delta$-alumina, $\theta$-alumina, $\kappa$-alumina, and boehmite.

In one aspect, the gamma-alumina may further include a rare earth element, an alkaline earth element, or a mixture of any two or more such elements. For example, the gamma-alumina may include a rare earth element. In particular embodiments, the rare earth element may be ytterbium, gadolinium, cerium, lanthanum, or a mixture of any two or more thereof. In particular embodiments, the rare earth element is lanthanum. In some embodiments, the gamma-alumina includes alkaline earth metals. In further embodiments, the alkaline earth metal is at least one of barium, calcium, or magnesium, or a mixture of any two or more thereof. In particular embodiments, the alkaline earth metal is barium.

In some embodiments, the rare earth or alkaline earth elements are present in an amount of from any of about 0.1 wt %, about 0.5 wt %, about 1 wt %, about 1.5 wt %, about 2 wt %, about 3 wt %, about 4 wt %, or about 5 wt % to any of about 6 wt %, about 7 wt %, about 8 wt %, about 9 wt %, about 10 wt %, about 11 wt %, or about 12 wt %, based on total weight of the gamma-alumina. In certain embodiments, the rare earth or alkaline earth elements are present in an amount of about 0.1 wt % to about 12 wt %, based on total weight of the gamma-alumina. In some embodiments, the rare earth or alkaline earth elements are present in an amount of about 1 wt % to about 10 wt %, based on total weight of the gamma-alumina. In a particular embodiment, the gamma-alumina includes about 1 wt % to about 5 wt % lanthanum. In a particular embodiment, the gamma-alumina includes about 1 wt % to about 3 wt % lanthanum. In particular embodiments, the gamma-alumina includes about 1 wt % to about 5 wt % barium. In a particular embodiment, the gamma-alumina includes about 1 wt % to about 3 wt % barium.

In some embodiments, the gamma-alumina, $\chi$-alumina, $\delta$-alumina, $\theta$-alumina, $\kappa$-alumina, or boehmite may further include a rare earth element, an alkaline earth element, or a mixture of any two or more such elements as described herein in any embodiment. For example, the gamma-alumina, $\chi$-alumina, $\delta$-alumina, $\theta$-alumina, $\kappa$-alumina, or boehmite in the catalyst may include a rare earth element, including but not limited to, ytterbium, gadolinium, cerium, lanthanum, or a mixture of any two or more thereof. In particular embodiments, the rare earth element may include lanthanum. In some embodiments, the gamma-alumina, $\chi$-alumina, $\delta$-alumina, $\theta$-alumina, $\kappa$-alumina, or boehmite in the catalyst may include an alkaline earth element. In some embodiments, the alkaline earth element may include barium, calcium, magnesium, or a mixture of any two or more thereof. In particular embodiments, the alkaline earth metal includes barium. In particular embodiments, the rare earth elements or alkaline earth elements are present in an amount of about 0.1 wt % to about 12 wt %, about 1 wt % to about 10 wt %, about 1% to about 5 wt %, or about 1 wt % to about 3 wt %, based on total weight of the gamma-alumina.

The first component (e.g., first microspheroidal FCC catalyst) may have a phase composition including at least about 10 wt %, at least about 15 wt %, at least about 20 wt %, at least about 30 wt %, at least about 35 wt %, at least about 40 wt %, at least about 45 wt %, at least about 50 wt %, at least about 55 wt %, at least about 60 wt %, at least about 65 wt %, at least about 70 wt %, at least about 75 wt %, or at least about 80 wt % Y zeolite, based on the total weight of the first component. In some embodiments, the first component (e.g., first microspheroidal FCC catalyst) may have a phase composition including at least 10 wt % Y zeolite. In some embodiments, the first component (e.g., first microspheroidal FCC catalyst) has a phase composition including at least 60 wt % Y zeolite. In some embodiments, the first component (e.g., first microspheroidal FCC catalyst)

may have a phase composition that includes at least about 30 wt % Y-zeolite. In some embodiments, the first component (e.g., first microspheroidal FCC catalyst) has a phase composition that includes at least about 40 wt % Y-zeolite. In particular embodiments, the first component (e.g., first microspheroidal FCC catalyst) has a phase composition that includes at least about 60 wt % Y-zeolite. In particular embodiments, the first component (e.g., first microspheroidal FCC catalyst) has a phase composition that includes at least about 65 wt % Y-zeolite.

The first component (e.g., first microspheroidal FCC catalyst) may further include mullite. In some embodiments, the first component (e.g., first microspheroidal FCC catalyst) may include about 5 wt % to about 40 wt % mullite. In some embodiments, the first component (e.g., first microspheroidal FCC catalyst) further includes at least about 20 wt % mullite.

The first component (e.g., first microspheroidal FCC catalyst) may have a phase composition including zeolite, mullite, and amorphous material. The first component (e.g., first microspheroidal FCC catalyst) may have a phase composition including Y-zeolite, mullite, and amorphous material. In some embodiments, the phase composition further may include at least about 30 wt % amorphous material.

The Y-zeolite may be crystallized as a layer on the surface of a first matrix, where the first matrix comprises gamma-alumina. In some embodiments, the first matrix also includes kaolin that has been subjected to calcination through an exotherm. In further embodiments, the first matrix includes about 20 wt % to about 60 wt % kaolin that has been subjected to calcination through an exotherm. In certain embodiments, the first matrix includes about 40 wt % kaolin that has been subjected to calcination through an exotherm. In certain embodiments, the first matrix includes about 30 wt % kaolin that has been subjected to calcination through an exotherm.

In some embodiments, the Y-zeolite of the first component (e.g., first microspheroidal FCC catalyst) may be ion-exchanged to reduce the sodium content of said first component to less than 0.7 wt %, less than 0.5 wt %, or less than 0.3 wt % $Na_2O$, based on total weight of the first component.

In some embodiments, the Y-zeolite may further include a rare earth element in the range of 0.1 wt % to 12 wt %, based on total weight of the first component. In some embodiments, the rare earth element may be lanthanum, cerium, praseodymium, neodymium, yttrium, or a mixture of any two or more. In particular embodiments, the rare earth element may be lanthanum. In certain embodiments, the rare earth element may be yttrium. In further particular embodiments, the Y-zeolite may be ion-exchanged to include the rare earth element. In some embodiments, the first component (e.g., first microspheroidal FCC catalyst) includes a lanthanum-exchanged zeolite crystallized in-situ in a porous kaolin matrix.

The first component (e.g., first microspheroidal FCC catalyst) may have a first matrix that comprises about 30 wt % gamma-alumina, about 30 wt % of kaolin that has been subjected to calcination through its characteristic exotherm, about 40 wt % metakaolin, based on total weight of the first component. In some embodiments, the gamma-alumina may be doped with a rare earth element such as lanthanum. In some embodiments, the first component (e.g., first microspheroidal FCC catalyst) includes at least about 20 wt % Y-zeolite crystallized in or on the matrix. In some embodiments, the Y-zeolite in the first component (e.g., first microspheroidal FCC catalyst) is ion-exchanged to reduce the sodium content of said catalyst is less than 0.3 wt % $Na_2O$, or less than about 0.2 wt % $Na_2O$, based on total weight of the first component. In some embodiments, the Y-zeolite further includes a rare-earth element such as lanthanum in the range of about 0.1 wt % to about 5 wt %, based on total weight of the first component.

In some embodiments, the Y-zeolite has a unit cell parameter of less than or equal to 24.75 Å. In some embodiments, the Y-zeolite has a unit cell parameter of less than or equal to 24.60 Å. In some embodiments, the Y-zeolite has a unit cell parameter of less than or equal to 24.55 Å. In some embodiments, the Y-zeolite has a unit cell parameter of from about 24.25 Å to about 24.70 Å.

In some embodiments, the first component's (e.g., first microspheroidal FCC catalyst's) average particle size may be from about 60 to about 100 micrometers. In some embodiments, the first component (e.g., first microspheroidal FCC catalyst) has an average particle size of about 60 to about 90 micrometers. In some embodiments, the first component (e.g., first microspheroidal FCC catalyst) has an average particle size of about 60 to about 80 micrometers.

In one aspect, methods of making the first component (e.g., first microspheroidal FCC catalyst) are described herein. In general, the active zeolitic component may be incorporated into the microspheres of the catalyst by one of two general techniques. In one technique, the zeolitic component is crystallized and then incorporated into microspheres in a separate step. In the second technique, the in-situ technique, microspheres are first formed and the zeolitic component is then crystallized in the microspheres themselves to provide microspheres containing both zeolitic and non-zeolitic components.

In one aspect, a method of making a zeolitic fluid catalytic cracking catalyst is provided, the method including: preforming precursor microspheres including a first matrix that may include a non-zeolitic material and gamma-alumina; and in-situ crystallizing zeolite Y inside the pre-formed microspheres to form the first microspheroidal FCC catalyst.

In some embodiments, the in-situ crystallization includes: mixing the pre-formed first precursor microspheres with sodium silicate, sodium hydroxide, and water to obtain an alkaline slurry; and heating the alkaline slurry to a temperature, and for a time, sufficient to crystallize at least about 10 wt %, at least about 15 wt %, at least about 20 wt %, at least about 25 wt %, at least about 30 wt %, at least about 35 wt %, at least about 40 wt %, or at least about 50 wt % of NaY-zeolite in or on the pre-formed first precursor microspheres, based on total weight of the pre-formed first precursor microspheres.

In some embodiments, the first matrix in the precursor microspheres may further include clay, rare earth-doped alumina (e.g., selected from one or more of ytterbium-doped alumina, gadolinium-doped alumina, cerium-doped alumina, or lanthanum-doped alumina), $SiO_2$—$Al_2O_3$ matrix, silica-doped alumina, χ-alumina, δ-alumina, θ-alumina, κ-alumina, boehmite or mixtures of two or more thereof. In particular embodiments, the first matrix in the precursor microspheres may include a mixture gamma-alumina and one or more of clay, rare earth-doped alumina (e.g., selected from one or more of ytterbium-doped alumina, gadolinium-doped alumina, cerium-doped alumina, or lanthanum-doped alumina), $SiO_2$—$Al_2O_3$ matrix, silica-doped alumina, χ-alumina, δ-alumina, θ-alumina, κ-alumina, and boehmite. In some embodiments, the first matrix in the precursor microspheres may include a mixture of gamma-alumina, χ-alumina, and one or more of clay, rare earth-doped alumina (e.g., selected from one or more of ytterbium-doped alumina, gadolinium-doped alumina, cerium-doped alumina, or lanthanum-doped alumina), SiO$_2$—Al$_2$O$_3$ matrix, silica-doped alumina, δ-alumina, θ-alumina, κ-alumina, and boehmite.

In some embodiments, a first zeolitic microspheroidal material may be isolated or separated from the crystallization liquor or from at least a major part of the alkaline slurry after contacting with water or another suitable liquid. The isolation may be carried out by commonly used methods such as filtration. In further embodiments, the first zeolitic microspheroidal material may be washed or contacted with water or other suitable liquid to remove residual crystallization liquor.

The method may further include mixing the first zeolitic microspheroidal material with an ammonium solution subsequent to contacting with the crystallization liquor, where the zeolitic microspheroidal material includes Y-zeolite in the sodium form prior to the mixing with the ammonium solution. In certain embodiments, the ammonium ions exchange at least some sodium ions in the first zeolitic microspheroidal material. In some embodiments, the mixing with the ammonium solution is conducted at acidic pH conditions. In some embodiments, the mixing with the ammonium solution is conducted at pH of about 3 to about 3.5. In some embodiments, the mixing with the ammonium solution is conducted at a temperature above room temperature. In some embodiments, the mixing with the ammonium solution is conducted at a temperature of at least about 80° C. to about 100° C., including increments therein.

In some embodiments, the ammonium exchanged first zeolitic microspheroidal material is further ion exchanged with a rare earth ion solution. In some embodiments, the rare earth ion are nitrates of lanthanum, cerium, praseodymium, neodymium, yttrium, or a mixture of any two or more such nitrates. In some embodiments, the microspheres are contacted with solutions of lanthanum nitrate. In some embodiments, the microspheres are contacted with solutions of yttrium nitrate. In one or more embodiments, the ion exchange step or steps are carried out so that the resulting first component contains less than about 0.3 wt % Na$_2$O, or less than about 0.2 wt % Na$_2$O. After ion exchange, the first zeolitic microspheroidal material is dried. Rare earth levels in the range of 0.1 wt % to 12 wt % by weight, specifically 1 wt %-5 wt %, and more specifically 2 wt %-3 wt % are contemplated. In certain embodiments, the amount of rare earth added to the first zeolitic microspheroidal material as a rare earth oxide will range from about 1 wt % to 5%, typically 2 wt %-3 wt % rare earth oxide (REO).

In some embodiments, the first zeolitic microspheroidal material is further calcined. In some embodiments, the calcining is conducted for at least about two hours. Such calcining may be conducted at a temperature of from about 500° C. to about 750° C. The calcination temperature, time, and order in the preparation process should not be construed as limiting. Under various circumstances, other calcination durations, temperatures, and order in the preparation process may be utilized. For instance, the calcination temperature may be lower than 500° C. or higher than 750° C. in certain embodiments. The calcination duration may be longer than two hours in certain embodiments. The calcination may occur after exchanging the first zeolitic microspheroidal material with ammonium ions or with ammonium ions and thereafter rare earth ions, before such an ion exchanging step, or both—before and after the ion exchanging step.

In another aspect, disclosed herein are first microspheroidal FCC catalysts as prepared by any of the methods disclosed herein.

The Y zeolite may be incorporated into a first matrix that includes gamma-alumina. In some embodiments, a slurry containing Y zeolite, gamma-alumina, and one or more binders is made and spray-dried to yield first microspheroidal FCC catalyst whose average particle size is from about 60 micrometers to about 100 micrometers. In some embodiments, the slurry further contains clay.

Alternatively, the first component (inclusive of Y-zeolite and a first matrix that includes gamma-alumina) may be produced into high zeolite content microspheres by the in-situ procedure described in U.S. Pat. No. 4,493,902 ("the '902 patent"). The '902 patent discloses FCC catalysts including attrition-resistant, high zeolitic content, catalytically active microspheres containing more than about 40%, preferably 50-70% by weight Y faujasite and methods for making such catalysts by crystallizing more than about 40% sodium Y-zeolite in porous microspheres composed of a mixture of metakaolin (kaolin calcined to undergo a strong endothermic reaction associated with dehydroxylation) and kaolin calcined under conditions more severe than those used to convert kaolin to metakaolin, i.e., kaolin calcined to undergo the characteristic kaolin exothermic reaction, sometimes referred to as the spinel form of calcined kaolin. The microspheres containing the two forms of calcined kaolin could also be immersed in an alkaline sodium silicate solution, which is heated, preferably until the maximum obtainable amount of Y faujasite is crystallized in the microspheres. The microspheres are separated from the sodium silicate mother liquor, ion-exchanged with rare earth, ammonium ions or both to form rare earth or various known stabilized forms of catalysts.

The first component (inclusive of Y-zeolite and a first matrix that includes gamma-alumina) may also be produced as Y-zeolite microspheres, which are disclosed in U.S. Pat. No. 6,656,347 ("the '347 patent") and U.S. Pat. No. 6,942,784 ("the '784 patent"). These Y-zeolite microspheres are macroporous, have sufficient levels of zeolite to be very active and are of a unique morphology to achieve effective conversion of hydrocarbons to cracked gasoline products with improved bottoms cracking under short contact time FCC processing. These zeolite microspheres are produced by a modification of technology described in the '902 patent.

Second Component

In one embodiment, the second component includes a beta zeolite and a second matrix. The second component may be a second microspheroidal FCC catalyst in certain embodiments though other catalyst shapes may also be suitably used. The second component is an incorporated catalyst.

The second component (e.g., second microspheroidal FCC catalyst) may be present in the FCC catalyst composition in an amount ranging from any of about 0.1 wt %, about 0.3 wt %, about 0.5 wt %, about 0.8 wt %, about 1 wt %, about 2 wt %, about 3 wt %, about 4 wt %, or about 5 wt % to any of about 6 wt %, about 7 wt %, about 8 wt %, about 9 wt %, about 10 wt %, about 12 wt %, about 15 wt %, or about 20 wt %, based on total weight of the FCC catalyst composition. In certain embodiments, the second component (e.g., second microspheroidal FCC catalyst) is present in the catalyst composition in an amount ranging from about 0.1 wt % to about 20 wt %, from about 1 wt % to about 15 wt %, from about 2 wt % to about 10 wt %, or any sub-range or single value therein, based on total weight of the FCC catalyst composition.

In some embodiments, the second component (e.g., second microspheroidal FCC catalyst) includes a phase composition that includes from any of about 1 wt %, about 3 wt %, about 5 wt %, about 8 wt %, about 10 wt %, about 15 wt %, about 20 wt %, or about 25 wt % to any of about 30 wt %, about 35 wt %, about 40 wt %, about 45 wt %, about 50 wt %, about 55 wt %, about 60 wt %, about 70 wt %, or about 80 wt %, beta zeolite, based on total weight of the second component. In certain embodiments, the second component includes at least about 10 wt % to about 60 wt %, about 15 wt % to about 55 wt %, about 20 wt % to about 50 wt %, or about 25 wt % to about 45 wt %, or any sub-range or single value therein, beta zeolite, based on total weight of the second component. In some embodiments, the second component includes phase composition of about 10 wt % to about 60 wt % beta zeolite, based on total weight of the second component. In some embodiments, the second component includes phase composition of about 15 wt % to about 55 wt % beta zeolite, based on total weight of the second component. In some embodiments, the second component includes about 25 wt % to about 45 wt % beta zeolite based on total weight of the second component. In some embodiments, the second component includes about 1 wt % to about 20 wt % beta zeolite, based on total weight of the second component. In some embodiments, the second component includes about 2 wt % to about 15 wt % beta zeolite, based on total weight of the second component. In some embodiments, the second component includes about 3 wt % to about 8 wt % beta zeolite, based on total weight of the second component.

In some embodiment described herein, the second component (e.g., second microspheroidal FCC catalyst) includes $AlPO_4$. Without being construed as limiting, it is believed that the $AlPO_4$ is formed due to the inclusion of boehmite during the preparation process of the second component. Without being construed as limiting, it is believed that, at constant oxidized phosphorus (e.g., $P_2O_5$) loading, increased amounts of boehmite could adversely affect the beta zeolite structure by scavenging P that might otherwise have stabilized the beta zeolite structure. It is also believed that the amount of boehmite contributes to the attrition resistance of the second component. In particular, it is believed that greater amounts of boehmite may enhance the attrition resistance of the second component. Hence, the amount of boehmite used in the preparation of the second component may be tuned to be sufficiently high to generate attrition resistant second component while not being too high de-stabilize or otherwise adversely affect the beta zeolite structure.

In certain embodiments, the boehmite amount added during the preparation of the second component is sufficient to form a second component having an air jet attrition rate (AJAR), as measured according to ASTM D 5757, that is less than about 5 wt %/hr, less than about 4.5 wt %/hr, or less than about 4 wt %/hr.

In certain embodiments, the amount of $AlPO_4$ in the second component may range from any of about 1 wt %, about 2 wt %, about 3 wt %, about 4 wt %, about 5 wt %, about 6 wt %, about 7 wt %, about 8 wt %, about 9 wt %, about 10 wt %, about 11 wt %, or about 12 wt % to any of about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, or about 25 wt %, based on total weight of the second component. In some embodiments, the amount of $AlPO_4$ in the second component ranges from about 1 wt % to about 25 wt %, from about 5 wt % to about 23 wt %, from about 10 wt % to about 20 wt %, or from about 13 wt % to about 17 wt %, or any sub-range or single value therein, based on total weight of the second component.

In some embodiments, the second component includes one or more of oxidized phosphorus (e.g., $P_2O_5$), phosphate treated component, or a silica-alumina binder. In one embodiment, the second component includes oxidized phosphorus (e.g., $P_2O_5$). In one embodiment, the second component includes a phosphate treated component. In one embodiment, the second component includes a silica-alumina binder.

Without being construed as limiting, it is believed that the binder type may indirectly contribute to the Brönsted acidity of the second component, which may be a reflection of the butylenes related activity of the second component. It was observed, in certain embodiments, that a second component that included oxidized phosphorus (e.g., $P_2O_5$) had a higher Brönsted acidity than a second component that included a silica-alumina binder. It was further observed, in certain embodiments, that a second component that included a silica-alumina binder had a higher Brönsted acidity than a second component that included P treated beta zeolite. In certain embodiments, the Brönsted acidity of the second component may range from about 10 μmol/g to about 65 μmol/g, from about 25 μmol/g to about 60 μmol/g, or about 35 μmol/g to about 55 μmol/g, or any sub-range or single value therein. In certain embodiments, the second component includes oxidized phosphorus (e.g., $P_2O_5$) and has a Brönsted acidity of about 35 μmol/g to about 55 μmol/g. In certain embodiments, the second component includes a silica-alumina binder and has a Brönsted acidity of about 25 μmol/g to about 40 μmol/g. In certain embodiments, the second component includes P treated beta zeolite and has a Brönsted acidity of about 10 μmol/g to about 25 μmol/g.

In certain embodiments, the second component includes oxidized phosphorus (e.g., $P_2O_5$) in an amount of from any of about 1 wt %, about 2 wt %, about 3 wt %, about 4 wt %, about 5 wt %, about 6 wt %, about 7 wt %, about 8 wt %, about 9 wt %, or about 10 wt % to any of about 11 wt %, about 12 wt %, about 13 wt %, about 14 wt %, about 15 wt %, about 16 wt %, about 17 wt %, about 18 wt %, about 19 wt %, or about 20 wt %, based on total weight of the second component. In certain embodiments, the second component includes oxidized phosphorus (e.g., $P_2O_5$) in an amount of about 1 wt % to about 30 wt %, about 2 wt % to about 25 wt %, about 5 wt % to about 20 wt %, or any sub-range or single value therein, based on total weight of the second component. Without being construed as limiting, it is believed that the inclusion of oxidized phosphorus (e.g., $P_2O_5$) in the second component reduces the amount/dose of second component required to give a 1 wt % of incremental increase in overall butylenes yield, as quantified upon contacting the second component with a hydrocarbon feed, when compared to the amount/dose required to generate a similar butylenes yield improvement with an identical second component that does not include oxidized phosphorus (e.g., $P_2O_5$).

In certain embodiments, the second component is substantially free of gamma-alumina. The term "substantially free," as used herein, refers to the second component having less than about 5 wt %, less than about 4 wt %, less than about 3 wt %, less than about 2 wt %, less than about 1 wt %, or 0 wt % gamma-alumina, based on the total weight of the second component. Without being construed as limiting, it is believed that the combination of beta zeolite, oxidized phosphorus such as $P_2O_5$ (or a different P based component), and gamma-alumina adversely effects/diminishes that performance of beta zeolite. Hence, in certain embodiments, the second component includes a combination of beta zeolite and $P_2O_5$ or a combination of beta zeolite and gamma-alumina but not the combination of P$_2$O$_5$ and gamma-alumina. In one embodiment, the second component includes beta zeolite and P$_2$O$_5$ while being substantially free of gamma-alumina. In one embodiment, the second component includes beta zeolite, gamma-alumina, and optionally a silica-alumina binder.

The silica to alumina ratio (SAR) in the beta zeolite in the second component ranges from any of about 20, about 25, about 30, or about 35 to any of about 40, about 50, about 75, about 100, about 150, about 200, about 250, or about 300. In certain embodiments, the SAR in the zeolite in the second component is from about 20 to about 300, from about 25 to about 100, from about 30 to about 50, or from about 30 to about 40. In certain embodiments, the second component is treated with phosphoric acid to bind oxidized phosphorus (e.g., P$_2$O$_5$) thereto and the beta zeolite has a SAR that is greater than about 30. Without being construed as limiting, it is believed that the SAR can be an important parameter which affects beta zeolite stability and activity. The SAR value should balance between maintaining the stability of the beta zeolite structure and the butylenes activity thereof.

The adverse effect on the beta zeolite may be evidenced by the zeolite surface area (ZSA) of the second component prior to steaming, the steamed zeolite surface area (SZSA) of the second component, and/or the comparison between the SZSA and the ZSA of the second component.

In certain embodiments, the ZSA of the second component ranges from any of about 50 m$^2$/g, about 75 m$^2$/g, about 100 m$^2$/g, about 110 m$^2$/g, or about 120 m$^2$/g to any of about 130 m$^2$/g, about 140 m$^2$/g, about 150 m$^2$/g, about 170 m$^2$/g, about 180 m$^2$/g, about 200 m$^2$/g, about 250 m$^2$/g, or about 300 m$^2$/g. In some embodiments, the ZSA of the second component ranges from about 50 m$^2$/g to about 300 m$^2$/g, from about 75 m$^2$/g to about 200 m$^2$/g, from about 100 m$^2$/g to about 180 m$^2$/g, from about 120 m$^2$/g to about 170 m$^2$/g, or from about 110 m$^2$/g to about 130 m$^2$/g, or any sub-range or single value therein.

In certain embodiments, the SZSA of the second component, after steaming in 100% steam at 1450° F. for 24 hours, ranges from any of about 50 m$^2$/g, about 60 m$^2$/g, about 70 m$^2$/g, about 75 m$^2$/g, about 80 m$^2$/g, about 90, or about 100 m$^2$/g, to any of about 110 m$^2$/g, about 120 m$^2$/g, about 130 m$^2$/g, about 140 m$^2$/g, about 150 m$^2$/g, about 170 m$^2$/g, about 180 m$^2$/g, about 200 m$^2$/g, about 250 m$^2$/g, or about 300 m$^2$/g. In some embodiments, the SZSA of the second component, after steaming in 100% steam at 1450° F. for 24 hours, ranges from about 50 m$^2$/g to about 300 m$^2$/g, from about 75 m$^2$/g to about 140 m$^2$/g, from about 90 m$^2$/g to about 120 m$^2$/g, or from about 100 m$^2$/g to about 110 m$^2$/g, or any sub-range or single value therein.

In certain embodiments, a majority of the ZSA of the second component is retained after steaming. For instance, at least about 65%, at least about 70%, at least about 75%, at least about 80%, at least about 85%, at least about 90%, or from about 80 to about 90%, of the ZSA of the second component is maintained after steaming in 100% steam at 1450° F. for 24 hours. Without being construed as limiting, it is believed that increasing the content of P$_2$O$_5$ in the second component improves beta zeolite structure retention, as evidenced at least by the comparison of SZSA to ZSA.

Without being construed as limiting, it is believed that the butylenes activity (quantified as amount of butylenes per dose of the second component that is generated upon contacting at least the second component with a hydrocarbon feed), increases with increasing oxidized phosphorus (e.g., P$_2$O$_5$) content and/or with increased ZSA and/or with increased SZSA.

In certain embodiments, the second component further includes kaolin. In certain embodiments, the second component includes beta zeolite in combination with kaolin, AlPO$_4$ formed from boehmite and phosphoric acid, and oxidized phosphorus (e.g., P$_2$O$_5$) while being substantially free of gamma-alumina.

In some embodiments, the second component's (e.g., second microspheroidal FCC catalyst's) average particle size may be from about 30 to about 250 micrometers. In some embodiments, the second component's (e.g., second microspheroidal FCC catalyst's) average particle size may be from about 60 to about 100 micrometers. In some embodiments, the second component (e.g., second microspheroidal FCC catalyst) has an average particle size of about 60 to about 90 micrometers. In some embodiments, the second component (e.g., second microspheroidal FCC catalyst) has an average particle size of about 60 to about 80 micrometers.

In certain embodiments, the second component (e.g., second microspheroidal FCC catalyst) may be formed by slurry blending beta zeolite with a second non-zeolitic material to form a slurry. The second non-zeolitic material may include boehmite alumina and kaolin in certain embodiments. In other embodiments, the second non-zeolitic material may include boehmite alumina, α-alumina, and kaolin. The process of forming the second component (e.g., second microspheroidal FCC catalyst) may also include spray drying the slurry.

In certain embodiments, the process of forming the second component (e.g., second microspheroidal FCC catalyst) may also include adding (e.g., injecting) phosphoric acid (H$_3$PO$_4$) during the spray drying.

As indicated earlier, the amount of boehmite and the amount of phosphoric acid that is added during the preparation of the second component is tuned to generate a second component that maintains its zeolite structure (evidenced by ZSA and SZSA), maintains its attrition resistance (evidenced by AJAR), and maintains its activity (evidenced by total butylenes yield). In certain embodiments, the amount of boehmite added to the slurry ranges from any of about 1 wt %, about 2 wt %, about 3 wt %, about 4 wt %, or about 5 wt % to any of about 6 wt %, about 7 wt %, about 8 wt %, about 9 wt %, or about 10 wt %, based on total weight of the slurry. In some embodiments, the amount of boehmite added to the slurry is from about 1 wt % to about 10 wt %, from about 3 wt % to about 9 wt %, or from about 5 wt % to about 8 wt %, or any sub-range or single value therein, based on the total weight of the slurry.

In certain embodiments, the process of forming the second component (e.g., second microspheroidal FCC catalyst) includes calcining the spray dried, and optionally oxidized phosphorus (e.g., P$_2$O$_5$) containing, second microspheroidal FCC catalyst material, to form the second microspheroidal FCC catalyst. In some embodiments, the calcining is conducted for at least about two hours. Such calcining may be conducted at a temperature of from about 500° C. to about 900° C., or about 700° C. The calcination temperature and duration should not be construed as limiting. Under various circumstances, other calcination durations and temperatures may be utilized.

The method may further include steam-treating the second microspheroidal FCC catalyst. In some embodiments, the steam-treating conducted at a temperature of at least about 700° C. In some embodiments, the steam-treating is conducted for at least about four hours. In some embodiments, the steam-treating is conducted for about one to about 24 hours. The steam treatment temperature and duration should not be construed as limiting. Under various circumstances, other steam treatment durations and temperatures may be utilized.

FCC Catalyst Composition

In certain embodiments, the instant disclosure is directed to an FCC catalyst composition that includes any of the first components described herein in combination with any of the second components described herein. The first component and the second component may be separate, such as a first microspheroidal FCC catalyst and a second microspheroidal FCC catalyst. The first microspheroidal FCC catalyst could include Y zeolite and a first matrix that includes gamma-alumina and the second microspheroidal FCC catalyst could include beta zeolite and a second matrix. In certain embodiments, the first component and the second component may be together incorporated into a common FCC catalyst (e.g., a common microspheroidal FCC catalyst) that includes Y zeolite, beta zeolite, and a matrix that includes gamma-alumina.

When the composition includes the first component and the second component as two separate constituents (e.g., a first microspheroidal FCC catalyst and a second microspheroidal FCC catalyst), the FCC catalyst composition may be formed by blending or mixing (e.g., physically mixing) any of the first components described hereinbefore and any of the second components described hereinbefore.

Any of the first components described herein may be added to the FCC catalyst composition in an amount ranging from any of about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, or about 90 wt %, based on total weight of the FCC catalyst composition. In certain embodiments, the first component (e.g., first microspheroidal FCC catalyst) is added to the FCC catalyst composition in an amount ranging from about 10 wt % to about 90 wt %, from about 30 wt % to about 80 wt %, from about 50 wt % to about 70 wt %, or any sub-range or single value therein, based on total weight of the FCC catalyst composition.

Any of the second components described herein may be added to the FCC catalyst composition in an amount ranging from any of about 0.1 wt %, about 0.3 wt %, about 0.5 wt %, about 0.8 wt %, about 1 wt %, about 2 wt %, about 3 wt %, about 4 wt %, or about 5 wt % to any of about 6 wt %, about 7 wt %, about 8 wt %, about 9 wt %, about 10 wt %, about 12 wt %, about 15 wt %, or about 20 wt %, based on total weight of the FCC catalyst composition. In certain embodiments, the second component (e.g., second microspheroidal FCC catalyst) may be added to the FCC catalyst composition in an amount ranging from about 0.1 wt % to about 20 wt %, from about 1 wt % to about 15 wt %, from about 2 wt % to about 10 wt %, or any sub-range or single value therein, based on total weight of the FCC catalyst composition.

In certain embodiments, the amount of the first component in the FCC catalyst composition is greater than the amount of the second component. For instance, the wt:wt ratio of the first component to the second component in the FCC catalyst composition may range from about 10:1 to about 1.5:1, from about 8:1 to about 2:1, or from about 4:1 to about 3:1. It is believed, without being construed as limiting, that such ratios contribute to improved conversion, butylenes to propylene selectivity ratio, and total butylenes yield, while maintaining or reducing the yield and/or selectivity of less desired products, such as coke and bottoms.

When the FCC catalyst composition includes the first component and the second component as two separate constituents (e.g., a first microspheroidal FCC catalyst and a second microspheroidal FCC catalyst), the second component with the beta zeolite may, in certain embodiments, refrain from combining gamma-alumina and a P-based constituent (such as oxidized phosphorus (e.g., $P_2O_5$)). In other words, as described above, in certain embodiments, the second component may include either beta zeolite with a P-based constituent (such as oxidized phosphorus (e.g., $P_2O_5$)) or beta zeolite with gamma-alumina, but not both, P-based constituent (such as oxidized phosphorus (e.g., $P_2O_5$)) and gamma-alumina simultaneously.

In certain embodiments, if the beta zeolite is combined with gamma-alumina (for example, when the Y zeolite, beta zeolite, and gamma-alumina are incorporated in a common catalyst), such component may be substantially free of a P-based constituent (such as oxidized phosphorus (e.g., $P_2O_5$)). The term "substantially free," as used herein, refers to the common catalyst having less than about 5 wt %, less than about 4 wt %, less than about 3 wt %, less than about 2 wt %, less than about 1 wt %, or 0 wt % added P-based constituent (such as oxidized phosphorus (e.g., $P_2O_5$)), based on the total weight of the common catalyst.

In certain embodiments, the FCC catalyst composition may further include at least one additional component that is compositionally different from the first component and from the second component. The at least one additional component may be a third microspheroidal FCC catalyst, a fourth microspheroidal FCC catalyst, and so on.

In certain embodiments, the at least one additional component may include (1) large pore zeolites (e.g., those having pore openings greater than about 7 Angstroms) such as, for example, USY, REY, silicoaluminophosphates SAPO-5, SAPO-37, SAPO-40, MCM-9, metalloaluminophosphate MAPO-36, aluminophosphate VPI-5, or mesoporous crystalline material MCM-41; REUSY, zeolite Z, zeolite Y, dealuminated zeolite Y, silica-enriched dealuminated zeolite Y, zeolite Beta, ZSM-3, ZSM-4, ZSM-18 and ZSM-20, (2) medium pore zeolites (e.g., those having pore openings of from about 4 Angstroms to about 7 Angstroms) such as, for example, ZSM-5, MCM-68, ZSM-11, ZSM-5, ZSM-11 intermediates, ZSM-12, ZSM-22, ZSM-23, ZSM-35, ZSM-38, ZSM-48, ZSM-57 silicoaluminophosphate SAPO-31 and (3) small pore zeolites (e.g., those having pore openings of less than about 4 Angstroms) such as, for example, erionite and ZSM-34.

In certain embodiments, the at least one additional component may include zeolite A, zeolite B, zeolite F, zeolite H, zeolite K-G, zeolite L, zeolite M, zeolite Q, zeolite R, zeolite T, mordenite, erionite, offretite, ferrierite, chabazite, clinoptilolite, gmelinite, phillipsite and faujasite.

Hydrothermally and/or chemically modified versions of many of the components described above may also be suitable as the at least one additional component in the FCC catalyst compositions contemplated herein.

In some embodiments, the at least one additional component may include at least one zeolite selected from ZSM-5, mordenite, ferrierite, MCM-22, MCM-68, Y-zeolite, beta zeolite, or a combination of two or more thereof. In one embodiment, the at least one additional component includes ZSM-5 zeolite.

When the FCC catalyst composition includes at least one additional component, the FCC catalyst composition may be prepared by blending any of the first components described herein, any of the second components described herein, and any of the at least one additional components described herein at their corresponding concentrations as also described herein.

In certain aspects, the instant disclosure is directed to a method of cracking a hydrocarbon feed by contacting said feed with any of the FCC catalyst compositions described in this disclosure. For instance, in certain embodiments, the method of cracking a hydrocarbon feed includes contacting said feed with an FCC catalyst composition that includes a first component (including Y zeolite and a first matrix including gamma-alumina) and a second component (including beta zeolite).

In certain embodiments, the methods of cracking a hydrocarbon feed, as described herein, result in an average butylenes to propylene selectivity ratio that is greater than about 0.7, greater than about 0.8, greater than about 0.85, greater than about 0.9, or greater than about 0.95, or about 1. In one embodiment, the method of cracking a hydrocarbon feed, as described herein, results in an average butylene to propylene selectivity ratio that is greater than about 0.7. In one embodiment, the method of cracking a hydrocarbon feed, as described herein, results in an average butylenes to propylene selectivity ratio that is greater than about 0.8. In one embodiment, the method of cracking a hydrocarbon feed, as described herein, results in an average butylenes to propylene selectivity ratio that is greater than about 0.85. In one embodiment, the method of cracking a hydrocarbon feed, as described herein, results in an average butylenes to propylene selectivity ratio that is greater than about 0.9. In one embodiment, the method of cracking a hydrocarbon feed, as described herein, results in an average butylenes to propylene selectivity ratio that is greater than about 0.95. In one embodiment, the method of cracking a hydrocarbon feed, as described herein, results in an average butylenes to propylene selectivity ratio that is about 1.

The butylenes activity of each component may be assessed from a total butylenes versus component dose plot. The slope of the total butylenes versus component dose plot may be used to interpolate the component dosage required to obtain a certain weight percent (e.g., 0.5 wt % or 1 wt %) incremental butylenes increase. The butylenes activity of the component that is being assessed is proportional to the reciprocal of that dosage. The butylenes to propylene selectivity ratio may be assessed from the slope of the total butylenes (TC4=in wt %) versus propylene (C3=in wt %) plot.

In certain embodiments, the methods of cracking a hydrocarbon feed, as described herein, maintain an average butylenes to propylene selectivity ratio that is within about 5%, within about 10%, or within about 15% of the average butylenes to propylene selectivity ratio obtained when contacting the feed with a comparative FCC catalyst composition that includes the first component (e.g., containing zeolite Y and gamma alumina) without the second component (e.g., containing beta zeolite). In one embodiment, the method of cracking a hydrocarbon feed, as described herein, maintains an average butylenes to propylene selectivity ratio that is within about 5% of the average butylenes to propylene selectivity ratio obtained when contacting the feed with a comparative FCC catalyst composition that includes the first component (e.g., containing zeolite Y and gamma alumina) without the second component (e.g., containing beta zeolite). In one embodiment, the method of cracking a hydrocarbon feed, as described herein, maintains an average butylenes to propylene selectivity ratio that is within about 10% of the average butylenes to propylene selectivity ratio obtained when contacting the feed with a comparative FCC catalyst composition that includes the first component (e.g., containing zeolite Y and gamma alumina) without the second component (e.g., containing beta zeolite). In one embodiment, the method of cracking a hydrocarbon feed, as described herein, maintains an average butylene to propylene selectivity ratio that is within about 15% of the average butylene to propylene selectivity ratio obtained when contacting the feed with a comparative FCC catalyst composition that includes the first component (e.g., containing zeolite Y and gamma alumina) without the second component (e.g., containing beta zeolite). This is a substantial improvement over ZSM-5 additives which degrade the base catalyst selectivity ratio substantially.

In certain embodiments, the methods of cracking a hydrocarbon feed, as described herein, result in increase in the total butylenes of greater than about 0.2 wt %, greater than about 0.3 wt %, greater than about 0.4 wt %, or greater than about 0.5 wt %, when compared to the total butylenes generated upon contacting the feed with a comparative FCC catalyst composition that includes the first component (e.g., containing zeolite Y and gamma alumina) without the second component (e.g., containing beta zeolite). In certain embodiments, the method of cracking a hydrocarbon feed, as described herein, results in increase in the total butylenes of greater than about 0.2 wt % when compared to the total butylenes generated upon contacting the feed with a comparative FCC catalyst composition that includes the first component (e.g., containing zeolite Y and gamma alumina) without the second component (e.g., containing beta zeolite). In certain embodiments, the method of cracking a hydrocarbon feed, as described herein, results in increase in the total butylenes of greater than about 0.3 wt % when compared to the total butylenes generated upon contacting the feed with a comparative FCC catalyst composition that includes the first component (e.g., containing zeolite Y and gamma alumina) without the second component (e.g., containing beta zeolite). In certain embodiments, the method of cracking a hydrocarbon feed, as described herein, results in increase in the total butylenes of greater than about 0.4 wt % when compared to the total butylenes generated upon contacting the feed with a comparative FCC catalyst composition that includes the first component (e.g., containing zeolite Y and gamma alumina) without the second component (e.g., containing beta zeolite). In certain embodiments, the method of cracking a hydrocarbon feed, as described herein, results in increase in the total butylenes of greater than about 0.5 wt % when compared to the total butylenes generated upon contacting the feed with a comparative FCC catalyst composition that includes the first component (e.g., containing zeolite Y and gamma alumina) without the second component (e.g., containing beta zeolite).

In certain embodiments, the method of cracking a hydrocarbon feed, as described herein, results in constant or lower bottoms versus coke selectivity ratio when compared to the bottoms versus coke selectivity ratio upon contacting the feed with a comparative FCC catalyst composition that includes the first component (e.g., containing zeolite Y and gamma alumina) without the second component (e.g., containing beta zeolite).

In certain embodiments, the method of cracking a hydrocarbon feed, as described herein, results in improved butylenes activity without compromising the butylenes to propylene selectivity ratio and the selectivity of less desired products (such as bottoms and coke), when compared to a comparative FCC catalyst composition that includes the first component (e.g., containing zeolite Y and gamma alumina) without the second component (e.g., containing beta zeolite).

In certain embodiments, the dose of second component required in the FCC catalyst composition, to increase the total butylenes upon cracking a hydrocarbon feed, ranges from about 1 wt % to about 15 wt %, from about 2 wt % to about 13 wt %, or from about 3 wt % to about 10 wt %.

In certain embodiments, the butylenes activity of the second component ranges from about 0.02 to about 0.15, from about 0.04 to about 0.14, or from about 0.05 to about 0.13. The butylenes activity is calculated as the amount of butylenes divided by the dose of the second component.

ILLUSTRATIVE EXAMPLES

The following examples are set forth to assist in understanding the disclosure and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1: Preparing a First Component

A first component was prepared as described herein and as described in U.S. Patent Application Publication No. US 2020/0078774, Example 1, which is incorporated herein in its entirety.

As described in US 2020/0078774, bottoms conversion increases with increasing gamma-alumina addition. Furthermore, as described in US 2020/0078774, the gamma-alumina is believed to provide a more favorable matrix activity and pore structure that improves bottoms upgrading without increasing coke yield compared to conventional clay based matrixes. It is also believed, as described in US 2020/0078774, that the increased matrix acidity of the La doped gamma alumina improved bottoms upgrading.

Hence, a first component that contains Y zeolite and gamma-alumina (in particular La doped gamma alumina) was contemplated as a suitable based FCC catalyst for an FCC catalyst composition designed to provide enhanced butylenes yield and activity at a constant or reduced yield or selectivity towards less desired products, such as coke.

Example 2: Preparing a Second Component

A second component was prepared as described in U.S. Pat. No. 9,227,181 (e.g., in column 9, line 23 through column 10, line 24), which is incorporated herein by reference in its entirety.

Second microspheroidal FCC catalysts (beta zeolite microspheres) with various binders were evaluated to determine the dose required for producing 0.5 wt % and 1 wt % incremental increase in total butylenes (TC4=) by ACE doping. ACE doping was used to assess the activity and selectivity of the beta zeolite microspheres. ACE doping was done at constant base catalyst/oil ratio, but with increasing levels of beta zeolite microspheres, and measuring the resulting incremental yields of butylenes and propylene. The microspheres contained 40 wt % of beta zeolite. The binders that were evaluated included boehmite and phosphoric acid ($H_3PO_4$) which ultimately formed $AlPO_4$, silica-alumina binder with ammonium phosphate treatment which may also be referred to herein as a "phosphate treated component" (PT, U.S. Pat. No. 8,940,652 B2), and silica alumina binder without ammonium phosphate treatment ($SiO_2$). The results are summarized in Table 1.

TABLE 1

40 wt % Beta Zeolite Microspheres Dosage for Producing 0.5 wt % and 1 wt % of Incremental Total Butylenes (TC4=) by ACE Doping

| | Dose for 0.5 wt % TC4 = increase | Dose for 1 wt % TC4 = increase | Wt % beta crystal in FCC | Brönsted acidity (µmol/g) |
|---|---|---|---|---|
| Boehmite + $H_3PO_4$ ($AlPO_4$) | 3.95-7.20% | 9-16% | 3.9-6.2% | 40-60 |
| PT | 9-18.4% | 37% | 15% | 15-25 |
| $SiO_2$ | 7-24.4% | 49% | 20% | 25-40 |

The results in Table 1 show that the boehmite and phosphoric acid binder ($AlPO_4$) reduced the required additive dose (i.e., required amount of beta zeolite microspheres) for producing a 0.5 wt % and 1 wt % of incremental increase in total butylenes yield (TC4=) and improved the butylenes activity and increased Brönsted acidity values. This has the advantage of forming a more economical second microspheroidal FCC catalyst as it would allow usage of a lower amount of the second microspheroidal FCC catalyst in the FCC catalyst composition, while also utilizing a lower zeolite beta crystal in the catalyst composition.

Example 3: Effect of Boehmite and $P_2O_5$ on Attrition and Butylene Activity in Second Component The effect of $P_2O_5$ and boehmite on butylene activity and attrition of the second component was evaluated by varying boehmite and $P_2O_5$ simultaneously in a statistically designed experiment. Samples with boehmite content of 3.5 wt %, 4.5 wt %, and 5.5 wt % were tested over a range of 10.2 to 12.7 wt % $P_2O_5$. As can be seen in Table 2 and in the FIGURE, lowering the boehmite content affected the attrition of the second component, evidenced by increased air jet attrition rate (AJAR) and air jet index (AJI). Statistical analysis showed that the attrition resistance could be fitted with a simple quadratic in VF boehmite, and that $P_2O_5$ played no discernable role. There was also no statistically significant variation in butylenes over the range studied.

TABLE 2

Effect of Boehmite and $P_2O_5$ on Attrition and Butylene Activity in Second Component

| Sample | Boehmite (wt %) | $P_2O_5$ (wt %) | AJI | AJAR | D50 | ZSA | SZSA | % ZSA retained |
|---|---|---|---|---|---|---|---|---|
| 1 | 4.50 | 12.73 | 8.8 | 2.0 | 91 | 143 | 126 | 88% |
| 2 | 3.50 | 12.09 | 18.9 | 4.4 | 84 | 142 | 127 | 90% |

TABLE 2-continued

Effect of Boehmite and $P_2O_5$ on Attrition
and Butylene Activity in Second Component

| Sample | Boehmite (wt %) | $P_2O_5$ (wt %) | AJI | AJAR | D50 | ZSA | SZSA | % ZSA retained |
|---|---|---|---|---|---|---|---|---|
| 3 | 5.50 | 10.46 | 7.1 | 1.6 | 87 | 159 | 121 | 76% |
| 4 | 4.50 | 10.99 | 8.0 | 1.8 | 87 | 153 | 124 | 81% |
| 5 | 5.50 | 11.58 | 6.0 | 1.3 | 83 | 156 | 126 | 80% |
| 6 | 3.50 | 10.16 | 17.4 | 4.0 | 87 | 153 | 123 | 81% |

Example 4: Blending First Component and Second Component

Several FCC catalyst compositions were modeled to assess their butylenes activity. The FCC catalyst compositions are shown in Table 3. The resulting yield projections are summarized in Table 4 below. The projected TC4=yields of FCC catalyst composition formulations were compared at a similar conversion. Comparative composition 1 may be compared to inventive composition 1 since both has 1.5 wt % rare earth oxides (REO). Comparative composition 2 may be compared to inventive composition 2 since both has 2.0 wt % rare earth oxides (REO). It can be seen from Table 4, that the inventive FCC catalyst compositions result in increased TC4=yield while maintaining a constant coke yield and a substantially similar butylenes to propylene selectivity ratio.

TABLE 3

FCC Catalyst Composition Formulations

| | Comparative Composition 1 (1.5 wt % REO) | Comparative Composition 2 (2.0 wt % REO) | Inventive Composition 1 (1.5 wt % REO) | Inventive Composition 2 (2.0 wt % REO) |
|---|---|---|---|---|
| First component (wt %) | 0 | 0 | 30 | 30 |
| Second component (wt %) | 8 | 8 | 8 | 8 |

TABLE 4

FCC Catalyst Compositions

| | Comparative Composition 1 (1.5 wt % REO) | Comparative Composition 2 (2.0 wt % REO) | Inventive Composition 1 (1.5 wt % REO) | Inventive Composition 2 (2.0 wt % REO) |
|---|---|---|---|---|
| Activity (MAT %) | 76.0 | 76.0 | 76.0 | 76.0 |
| Conversion (Vol %) | 83.95 | 83.53 | 84.44 | 84.11 |
| Product Yields (wt % Basis) | | | | |
| Propane | 2.70 | 2.75 | 2.77 | 2.74 |
| Propylene | 10.08 | 9.99 | 10.18 | 10.14 |
| N-Butane | 1.31 | 1.32 | 1.37 | 1.35 |
| Isobutane | 6.38 | 6.46 | 6.59 | 6.50 |
| 1-Butene | 1.85 | 1.77 | 1.89 | 1.86 |
| C-2-Butene | 1.59 | 1.52 | 1.62 | 1.60 |
| T-2-Butene | 2.50 | 2.39 | 2.56 | 2.52 |
| Isobutene | 4.06 | 3.82 | 4.16 | 4.01 |
| Butadiene | 0.09 | 0.07 | 0.10 | 0.10 |
| Total C4 Olefins | 10.00 | 9.50 | 10.22 | 9.98 |
| Total C3 + C4 | 30.56 | 30.10 | 31.23 | 30.81 |
| C5+ Gasoline (C5-450° F.) | 41.23 | 41.43 | 41.07 | 41.08 |
| Light Cycle Oil (450-680° F.) | 12.14 | 12.38 | 11.88 | 12.14 |
| Decant (680° F.+) | 5.73 | 5.93 | 5.46 | 5.53 |
| Coke | 6.21 | 6.21 | 6.21 | 6.22 |
| Delta Coke | 0.88 | 0.90 | 0.85 | 0.88 |
| Product Yields (vol % Basis) | | | | |
| Propane | 4.80 | 4.89 | 4.94 | 4.88 |
| Propylene | 17.46 | 17.30 | 17.63 | 17.55 |
| N-Butane | 2.02 | 2.05 | 2.11 | 2.09 |
| Isobutane | 10.24 | 10.37 | 10.58 | 10.44 |
| Total C4 Olefins | 14.97 | 14.20 | 15.31 | 14.95 |
| Total C3 + C4 | 49.49 | 48.81 | 50.57 | 49.90 |
| C5+ Gasoline (C5-450° F.) | 48.65 | 48.90 | 48.49 | 48.48 |

TABLE 4-continued

| | FCC Catalyst Compositions | | | |
|---|---|---|---|---|
| | Comparative Composition 1 (1.5 wt % REO) | Comparative Composition 2 (2.0 wt % REO) | Inventive Composition 1 (1.5 wt % REO) | Inventive Composition 2 (2.0 wt % REO) |
| Light Cycle Oil (450-680° F.) | 11.28 | 11.52 | 11.03 | 11.28 |
| Decant (680° F.+) | 4.77 | 4.95 | 4.53 | 4.60 |
| C3+ Liquid | 114.19 | 114.17 | 114.62 | 114.26 |

Example 5: Effect of Beta Zeolite Composition on Total C5=Olefin Yield

Several FCC catalyst compositions were modeled to assess their C5=olefin activity. The FCC catalyst compositions and resulting yield projections are shown and summarized in Table 5. The results were computed based on a statistical model for ACE yields developed by systematically varying first component properties, second component and/or ZSM-5 concentration, and dilution by inert components. Gasoline conversion was 70 wt %, the steamed zeolite surface area to matrix surface area ratio (Z/M) of the catalysts was 2.20, and the steamed unit cell size (SUCS) of the catalysts was 24.28 Å. Yields are given in weight percent, unless expressed as a ratio.

The yields include PIONA (paraffins, isoparaffins, olefins, naphthenes, aromatics) grouped analysis of the ACE liquid product only. Within the PIONA data are C5 olefins yields (excluding the cyclic C5 olefins), as well as octanes. While it is noted that this data was computed without the presence of Ni or V and without the catalyst composition including Ni or V passivators, it allows for a comparison of the effects of beta and ZSM-5 additives on a base catalyst formulation.

Increased amounts of beta zeolite resulted in an increase of total iso-olefins, with use of ZSM5 driving these totals down while driving aromatics and cyclic olefins up. The results also indicate an increase in total C5=olefin yield (i-C5=+n-C5=yield from PIONA analysis modeling) when compared to contacting the feed with an FCC catalyst composition that comprises Y zeolite without beta zeolite, as well as compared to contacting the feed with an FCC catalyst composition for which the second component is replaced with ZSM-5.

TABLE 5

| Yields Based on FCC Catalyst Composition | | | | | | | | | | | |
|---|---|---|---|---|---|---|---|---|---|---|---|
| | #1 | #2 | #3 | #4 | #5 | #6 | #7 | #8 | #9 | #10 | #11 |
| Beta (wt %) | 0.0 | 2.0 | 4.0 | 6.0 | 8.0 | 12.0 | 0.0 | 0.0 | 0.0 | 8.0 | 12.0 |
| ZSM-5 (wt %) | 0.0 | 0.0 | 0.0 | 0.0 | 0.0 | 0.0 | 2.0 | 4.0 | 6.0 | 2.0 | 6.0 |
| Yields | | | | | | | | | | | |
| Dry gas | 2.01 | 2.00 | 1.99 | 1.98 | 1.97 | 1.95 | 2.12 | 2.24 | 2.36 | 2.10 | 2.39 |
| Propane | 1.0 | 1.0 | 1.0 | 1.0 | 1.0 | 1.1 | 1.3 | 1.5 | 1.5 | 1.3 | 1.6 |
| Propylene | 5.3 | 5.4 | 5.4 | 5.5 | 5.6 | 5.7 | 7.3 | 8.7 | 9.5 | 7.6 | 10.2 |
| C3=/TC3 | 0.83 | 0.83 | 0.83 | 0.83 | 0.83 | 0.84 | 0.85 | 0.86 | 0.86 | 0.85 | 0.87 |
| TC4= | 6.94 | 6.97 | 7.03 | 7.14 | 7.27 | 7.65 | 7.84 | 8.50 | 8.92 | 8.17 | 9.63 |
| TC4=/TC4 | 0.60 | 0.59 | 0.59 | 0.59 | 0.60 | 0.61 | 0.60 | 0.61 | 0.61 | 0.60 | 0.63 |
| iC4=/iC4 | 0.56 | 0.55 | 0.55 | 0.56 | 0.58 | 0.64 | 0.59 | 0.63 | 0.67 | 0.62 | 0.75 |
| TC4=/C3= | 1.33 | 1.34 | 1.34 | 1.34 | 1.34 | 1.35 | 1.11 | 0.98 | 0.94 | 1.12 | 0.96 |
| LPG | 17.8 | 18.0 | 18.2 | 18.4 | 18.7 | 19.1 | 21.6 | 24.2 | 25.7 | 22.4 | 27.0 |
| Gasoline (C5 to 430° F.) | 48.1 | 47.9 | 47.6 | 47.4 | 47.2 | 46.7 | 44.2 | 41.4 | 39.8 | 43.3 | 38.4 |
| LCO (430 to 650° F.) | 17.8 | 17.8 | 17.8 | 17.7 | 17.7 | 17.6 | 17.8 | 17.7 | 17.7 | 17.6 | 17.4 |
| Bottoms (650 + above) | 12.2 | 12.2 | 12.2 | 12.3 | 12.3 | 12.4 | 12.2 | 12.3 | 12.3 | 12.4 | 12.6 |
| Coke | 2.105 | 2.1 | 2.1 | 2.1 | 2.1 | 2.1 | 2.1 | 2.1 | 2.1 | 2.1 | 2.1 |
| LPG Sats. | 5.7 | 5.8 | 5.9 | 5.9 | 5.9 | 5.9 | 6.5 | 7.1 | 7.3 | 6.8 | 7.3 |
| Butylenes | 6.9 | 7.0 | 7.1 | 7.2 | 7.3 | 7.6 | 7.8 | 8.5 | 8.9 | 8.2 | 9.6 |
| Delta Butylenes | 0.00 | 0.06 | 0.14 | 0.24 | 0.37 | 0.70 | 0.87 | 1.54 | 1.99 | 1.25 | 2.69 |
| i-C5= + n-C5= (PIONA) | 3.09 | 3.09 | 3.10 | 3.10 | 3.11 | 3.12 | 2.97 | 2.86 | 2.75 | 2.99 | 2.78 |
| PIONA | | | | | | | | | | | |
| total naph. | 8.95 | 8.89 | 8.83 | 8.77 | 8.70 | 8.58 | 9.43 | 9.62 | 9.52 | 9.19 | 9.14 |
| total i-par | 12.46 | 12.28 | 12.11 | 11.93 | 11.76 | 11.41 | 11.40 | 11.14 | 11.69 | 10.70 | 10.64 |
| total n-par | 2.18 | 2.21 | 2.23 | 2.24 | 2.23 | 2.18 | 1.92 | 1.78 | 1.74 | 1.97 | 1.75 |
| total cyclic olefins | 9.30 | 9.27 | 9.32 | 9.43 | 9.61 | 10.19 | 10.37 | 11.08 | 11.44 | 10.69 | 12.33 |
| total i-olefin | 16.02 | 16.23 | 16.44 | 16.65 | 16.86 | 17.28 | 14.01 | 12.60 | 11.79 | 14.69 | 12.35 |
| total n-olefin | 6.81 | 6.80 | 6.79 | 6.78 | 6.77 | 6.75 | 5.51 | 4.67 | 4.30 | 5.47 | 4.24 |
| total aromatics | 40.89 | 40.89 | 40.89 | 40.89 | 40.89 | 40.89 | 46.04 | 49.67 | 51.75 | 46.04 | 51.75 |
| other | 0.33 | 0.33 | 0.33 | 0.33 | 0.33 | 0.33 | 0.37 | 0.42 | 0.46 | 0.37 | 0.46 |
| benzene | 0.51 | 0.52 | 0.53 | 0.54 | 0.54 | 0.56 | 0.67 | 0.78 | 0.87 | 0.70 | 0.91 |
| i-C5= | 1.87 | 1.88 | 1.89 | 1.89 | 1.90 | 1.92 | 1.85 | 1.82 | 1.80 | 1.88 | 1.85 |
| i-C6= | 4.98 | 5.04 | 5.12 | 5.22 | 5.34 | 5.65 | 4.75 | 4.53 | 4.31 | 5.06 | 4.70 |

TABLE 5-continued

Yields Based on FCC Catalyst Composition

|  | #1 | #2 | #3 | #4 | #5 | #6 | #7 | #8 | #9 | #10 | #11 |
|---|---|---|---|---|---|---|---|---|---|---|---|
| i-C7= | 4.09 | 4.14 | 4.19 | 4.24 | 4.28 | 4.38 | 3.08 | 2.46 | 2.23 | 3.23 | 2.32 |
| i-C8= | 2.56 | 2.57 | 2.58 | 2.59 | 2.60 | 2.61 | 2.11 | 1.77 | 1.54 | 2.15 | 1.59 |
| n-C4= | 0.12 | 0.09 | 0.06 | 0.05 | 0.04 | 0.04 | 0.15 | 0.18 | 0.21 | 0.05 | 0.07 |
| n-C5= | 1.22 | 1.22 | 1.21 | 1.21 | 1.21 | 1.20 | 1.13 | 1.04 | 0.94 | 1.11 | 0.92 |
| n-C6= | 2.30 | 2.34 | 2.37 | 2.40 | 2.44 | 2.50 | 1.99 | 1.76 | 1.63 | 2.10 | 1.74 |
| n-C7= | 1.33 | 1.33 | 1.33 | 1.33 | 1.33 | 1.33 | 0.87 | 0.59 | 0.49 | 0.87 | 0.49 |
| n-C8= | 0.68 | 0.67 | 0.67 | 0.66 | 0.66 | 0.64 | 0.46 | 0.32 | 0.25 | 0.45 | 0.24 |
| RON | 94.56 | 94.72 | 94.89 | 95.05 | 95.21 | 95.53 | 96.16 | 97.29 | 97.97 | 96.80 | 98.93 |
| MON | 78.99 | 79.04 | 79.09 | 79.14 | 79.19 | 79.28 | 80.00 | 80.83 | 81.48 | 80.19 | 81.77 |
| Wt % Benzene | 0.58 | 0.59 | 0.60 | 0.61 | 0.62 | 0.63 | 0.75 | 0.87 | 0.95 | 0.78 | 1.00 |
| Wt % Toluene | 4.92 | 4.92 | 4.93 | 4.93 | 4.93 | 4.93 | 5.73 | 6.26 | 6.50 | 5.74 | 6.51 |
| (R + M)/2 | 86.86 | 86.94 | 87.01 | 87.09 | 87.16 | 87.31 | 88.17 | 89.15 | 89.81 | 88.47 | 90.27 |

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present disclosure has been described with reference to specific exemplary embodiments thereof. The specification and drawings are, accordingly, to be regarded in an illustrative rather than a restrictive sense. Various modifications of the disclosure in addition to those shown and described herein will become apparent to those skilled in the art and are intended to fall within the scope of the appended claims.

The invention claimed is:

1. A fluid catalytic cracking (FCC) catalyst composition comprising:
    a first component comprising Y zeolite and a first matrix comprising gamma-alumina; and
    a second component comprising beta zeolite and a second matrix, wherein the second component is present in the FCC catalyst composition in an amount ranging from about 0.1 wt % to about 20 wt % based on total weight of the FCC catalyst composition.

2. The FCC catalyst composition of claim 1, wherein the first component comprises an incorporated catalyst or an in-situ catalyst.

3. The FCC catalyst composition of claim 1, wherein the first component is a first microspheroidal FCC catalyst that is present in the FCC catalyst composition in an amount ranging from about 10 wt % to about 90 wt %, based on total weight of the FCC catalyst composition.

4. The FCC catalyst composition of claim 3, wherein the second component is a second microspheroidal FCC catalyst.

5. The FCC catalyst composition of claim 1, wherein the second component further comprises oxidized phosphorus and does not comprise gamma-alumina, or the second component further comprises gamma-alumina and does not comprise oxidized phosphorus.

6. The FCC catalyst composition of claim 1, wherein the second component further comprise one or more of oxidized phosphorus, a phosphate treated component, or a silica-alumina binder.

7. The FCC catalyst composition of claim 6, wherein the second component comprises about 1 wt % to about 30 wt % of $P_2O_5$, based on total weight of the second component.

8. The FCC catalyst composition of claim 7, wherein the second component is substantially free of gamma-alumina.

9. The FCC catalyst composition of claim 1, wherein the second matrix comprises kaolin.

10. The FCC catalyst composition of claim 1, wherein the silica to alumina ratio (SAR) in the beta zeolite ranges from about 20 to about 300.

11. The FCC catalyst composition of claim 1, wherein the zeolite surface area (ZSA) of the second component ranges from about 50 $m^2/g$ to about 300 $m^2/g$.

12. The FCC catalyst composition of claim 1, wherein the steamed zeolite surface area (SZSA) of the second component ranges from ranges from about 50 $m^2/g$ to about 300 $m^2/g$, after steaming in 100% steam at 1450° F. for 24 hours.

13. The FCC catalyst composition of claim 12, wherein at least about 65% of the ZSA of the second component is maintained after steaming in 100% steam at 1450° F. for 24 hours.

14. The FCC catalyst composition of claim 1, wherein the first matrix further comprises one or more of clay, rare earth-doped alumina, $SiO_2$—$Al_2O_3$ matrix, silica-doped alumina, $\chi$-alumina, $\delta$-alumina, $\theta$-alumina, $\kappa$-alumina, or boehmite.

15. The FCC catalyst composition of claim 1, wherein the gamma-alumina of the first matrix is doped with a rare earth element.

16. The FCC catalyst composition of claim 1, wherein the Y zeolite in the first component comprises Y zeolite that has been ion-exchanged to reduce sodium content to less than 0.7 wt %, or to less than 0.5 wt % $Na_2O$, based on total weight of the ion-exchanged Y zeolite.

17. The FCC catalyst composition of claim 1, wherein the Y zeolite in the first component comprises Y zeolite that has been ion exchanged to include a rare earth element.

18. The FCC catalyst composition of claim 1, further comprising
- at least one additional component that is compositionally different from the first component and from the second component,
- wherein the at least one additional component comprises a zeolite selected from ZSM-5, mordenite, ferrierite, MCM-22, MCM-68, or a combination thereof.

19. A method of making a fluid catalytic cracking (FCC) catalyst composition of claim 1, the method comprising blending the first component and the second component.

20. A method of cracking a hydrocarbon feed comprising contacting the hydrocarbon feed with the FCC catalyst composition of claim 1.

\* \* \* \* \*